United States Patent [19]

Wolf et al.

[11] Patent Number: 5,271,898

[45] Date of Patent: Dec. 21, 1993

[54] APPARATUS FOR TESTING BLOOD/BIOMATERIALS/DEVICE INTERACTIONS AND CHARACTERISTICS

[75] Inventors: Michael F. Wolf, Brooklyn Park; Paul V. Trescony, Champlin; James R. Keogh, Maplewood, all of Minn.

[73] Assignee: Medtronic, Inc., Minneapolis, Minn.

[21] Appl. No.: 56,450

[22] Filed: May 3, 1993

[51] Int. Cl.$^5$ .......................................... G01N 33/49
[52] U.S. Cl. ...................... 422/64; 422/73; 422/99; 436/52; 73/61.65
[58] Field of Search ............... 436/69, 52; 73/64.41, 73/61.65; 422/73, 99, 64, 132

[56] References Cited

U.S. PATENT DOCUMENTS

| | | | |
|---|---|---|---|
| 3,074,627 | 1/1963 | Goetz | 73/61.65 |
| 3,503,709 | 3/1970 | Yochem | 436/69 |
| 3,518,057 | 6/1970 | Giordano | 436/69 |
| 3,695,842 | 10/1972 | Mintz | 436/69 X |
| 3,766,774 | 10/1973 | Clark | 73/64.41 |
| 3,911,728 | 10/1975 | Fixot | 73/64.41 X |
| 4,081,242 | 3/1978 | Girolami | 436/69 X |
| 4,146,172 | 3/1979 | Cullis et al. | 233/26 |
| 4,663,127 | 5/1987 | Jackson et al. | 422/58 |
| 5,078,739 | 1/1992 | Martin | 623/2 |
| 5,151,105 | 9/1992 | Kwan-Gett | 623/1 |
| 5,156,600 | 10/1992 | Young | 604/247 |

OTHER PUBLICATIONS

"A Simple in Vitro Screening Test for Blood Compatability of Materials" by Kambic et al. in Journal of Biomedical Materials Research Symposium, No. 7, pp. 561–570 (1976).
"An in Vitro Test Model to Study the Performance and Thrombogenecity of Cardiovascular Devices" by Swier et al. in vol. XXXV Trans. Am. Soc. Artif. Intern. Organs 1989.
"A Physiological Approach to High-Frequency Testing of Prosthetic Ball Valves" by Almond et al. in The Journal of Thoracic and Cardiovascular Surgery, Jun., 1974.
"In Vitro and ex Vivo Platelet Interactions with Hydrophilic-Hydrophobix Poly(Ethylene Oxide)-Polystyrene Multiblock Copolymers" by Grainger, et al. in Journal of Biomedical Materials Research, vol. 23, 979–1005 (1989).
"Quantitative Ultrasonographic Studies of Lower Extremity Flow Velocities in Health and Disease" by A. Fronek, M. Coel and E. F. Bernstein in *Circulation*, vol. 53, No. 6, Jun., 1971 at p. 958.
"In Vitro Thrombotic Coagulation of the Blood" A Method for Producing a Thrombus, A. B. Chandler, M.D., Laboratory Investigation, pp. 110–114, 1958.
"An in Vitro Study of the Adhesion of Blood Platelets onto Vascular Catheters, Part I.", by Engbers et al. in Journal of Biomedical Materials Research, vol. 21, 613–627 (1987).
"The Role of Blood Flow in Platelet Adhesion, Fibrin Deposition, and Formation of Mural Thrombi" by Baugartner, in Microvascular Research 5, 167–179 (1973).
"The Platelet Reactivity of Vascular Graft Prosthesis: An In Vitro Model to Test the Effect of Preclotting" by Kottke-Marchant et al., in Biomaterials, 1986, vol. 7 Nov.
"Peripheral Circulation" in *Geigy Scientific Tables*, vol. 5, Heart and Circulation, 8th Revised and Enlarged Ed., at p. 226 published by Ciba-Geigy.
"Controlled-Flow Instruments for Simulating in Vivo Trombosis" by Clark et al. in Thrombos, Diathes, Haemorrh (Stuttg), 1973, 30, 519.
"Study of the Reactions of Blood with Artificial Surfaces", by Mason, et al. in journal Laboratory Investigation, vol. 31, No. 2, p. 143 (1974).

Primary Examiner—James C. Housel
Assistant Examiner—Harold Y. Pyon
Attorney, Agent, or Firm—Daniel W. Latham; Harold R. Patton

[57] ABSTRACT

An apparatus designed to test blood, blood contacting biomaterials and devices such as materials and surface-modified materials; vascular grafts, stents, heart valves, catheters, leads, etc., for blood and material responses in vitro under physiological blood flow conditions. The apparatus consists of a stepper-motor driven circular disc(s), upon which a test vehicle, containing either the test materials, coating or device, is mounted. The test vehicle itself consists of a circular, closed-loop of polymer tubing containing a check valve.

23 Claims, 4 Drawing Sheets

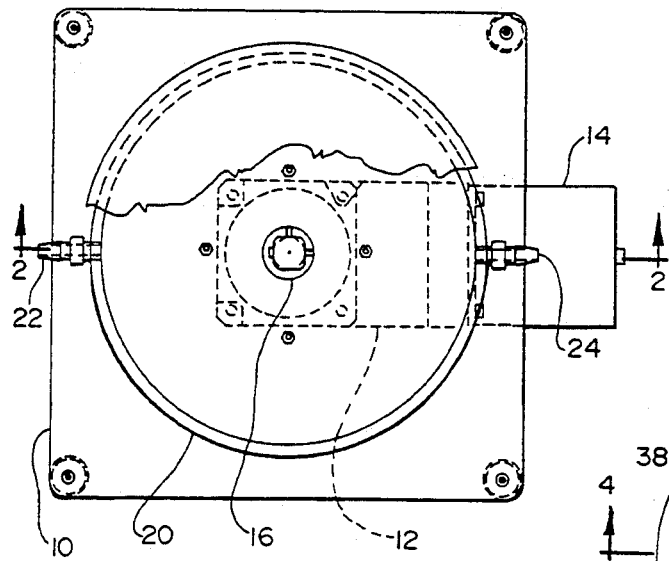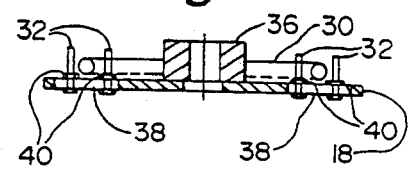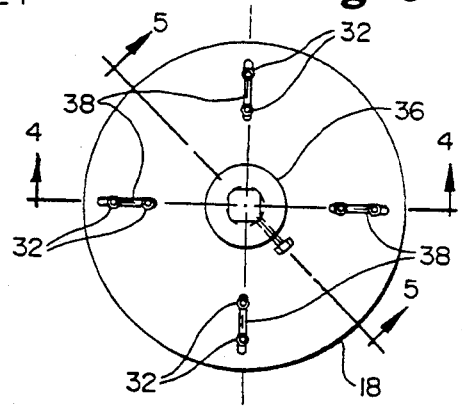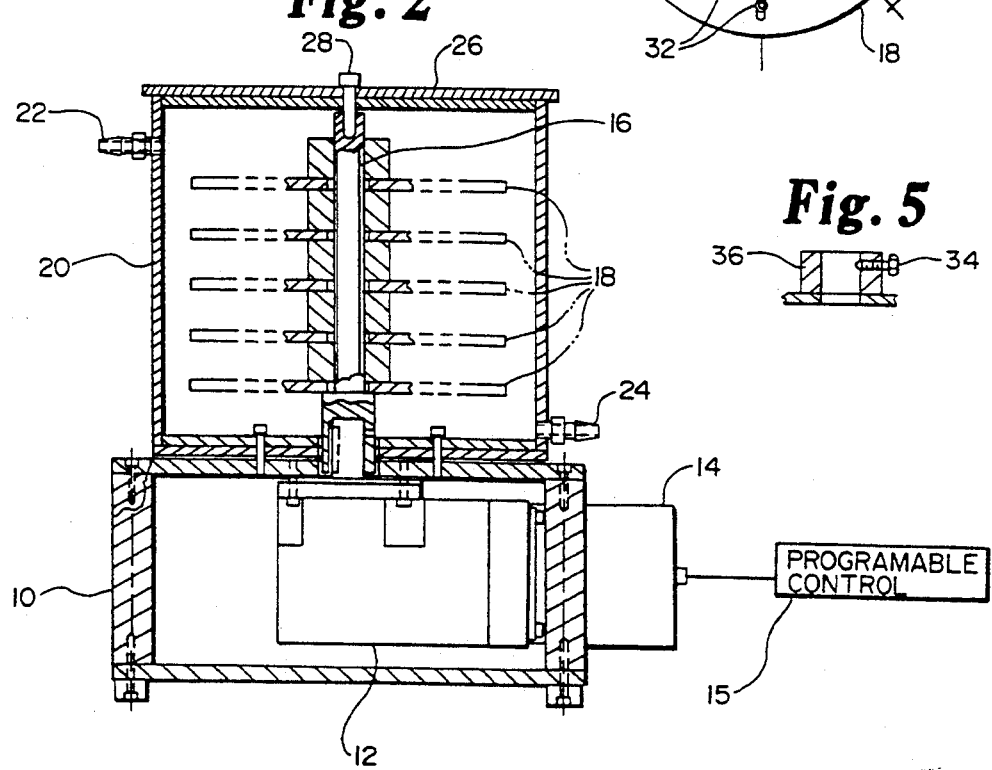

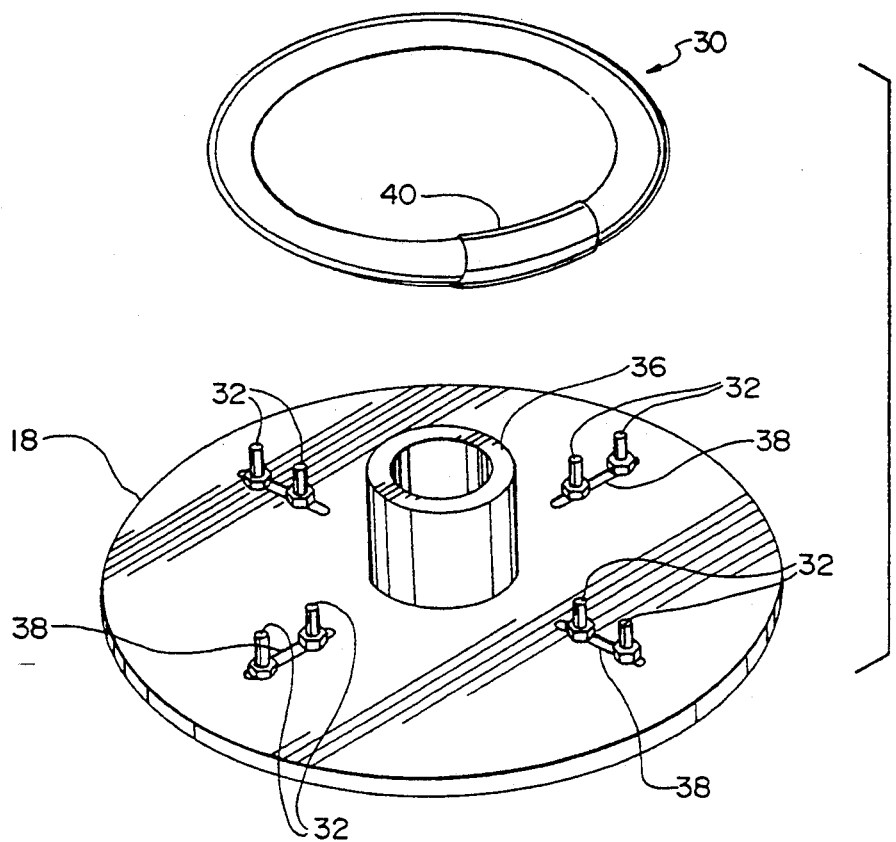
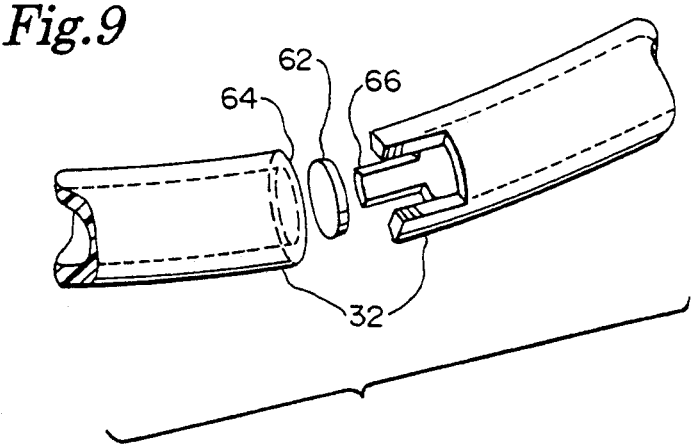

APPARATUS FOR TESTING BLOOD/BIOMATERIALS/DEVICE INTERACTIONS AND CHARACTERISTICS

BACKGROUND OF THE INVENTION

Field of the Invention

This invention is directed to improvements relating to devices intended to create an optimum environment for the in vitro study of dynamic blood-material (biomaterial surfaces, biomedical devices and the like) interactions. Interactions commonly measured include changes in the character of blood and changes that take place within or on materials, surfaces, devices and the like following interaction with flowing blood. Such a device is shown in U.S. Pat. No. 3,766,774 which issued to Howard G. Clark on Oct. 23, 1973, the subject matter of which is incorporated herein by reference.

In addition to the aforementioned patent, the Clark device is described in an article entitled Controlled Flow Instruments for Simulating In Vivo Thrombosis; by H. G. Clark, B. A. Shinoda and R. G. Mason which appeared in *Thrombos, Diathes, Haemorrh (Stuttg)*, 1973, 30, 519. It is also described in another article entitled Study of the Reactions of Blood With Artificial Surfaces-Use of the Thrombo Generator; by R. G. Mason, W. H. Zucker, B. A. Shinoda, H. Y. Chuang, H. S. Kingdon and H. G. Clark which appeared in volume 31, No. 2, at page 143 (1974), in the journal *Laboratory Investigation*. All of these articles are incorporated herein by reference also.

In the Clark apparatus, a continuous closed loop of tubing is filled with blood which is to undergo tests. The tubing is attached to the circumference of a balance wheel which is then oscillated about a fixed point. The inertia of the fluid in the oscillating tube causes the blood to tend to remain stationary about its location within the tube, leading to no net circulation of the blood within the tube. The oscillated closed loop thus creates some oscillatory shear-induced blood movement at the blood-wall interface and is thus intended to simulate pulsatile flow in the living circulatory system.

SUMMARY OF THE INVENTION

The invention improves the aforementioned apparatus in an variety of ways, chief among which is the introduction of a check valve in the blood test loop, i.e., the closed loop tubular test cell. As a result of the latter design modification, oscillatory motion about a fixed point and/or defined pulsed motion in either a clockwise (cw) or counter clockwise (ccw) direction will create net directional (cw or ccw) pulsatile flow to the fluid mass within the test cell. In addition, the apparatus is of a generally improved design including a programmable microstepper motor driven system for precise definition/control of rotational patterns designed to create physiological fluid flow profiles, a tiered arrangement for testing a plurality of closed loop test cells simultaneously, and a temperature control bath arrangement for closely controlling temperature during testing.

BRIEF DESCRIPTION OF THE DRAWINGS

A detailed description of the invention is hereafter described with specific reference being made to the drawings in which:

FIG. 1 is a plan view of the improved apparatus of the invention.

FIG. 2 is a cross-sectional view taken along line 2—2 of the apparatus shown in FIG. 1.

FIG. 3 is a plan view of a disc shaped tray which mounts the closed loop test cell in the apparatus.

FIG. 4 is a cross-sectional view taken along lines 4—4 of FIG. 3 showing the disc like tray with a test vehicle mounted thereon.

FIG. 5 is a cross-sectional view taken along lines 5—5 of FIG. 3 showing the means for mounting the test tray in the apparatus.

FIG. 8 is a pictorial representation of a test cell and test tray indicating how they are brought together for mounting in the apparatus.

FIG. 9 is a showing of a portion of a test cell and an alternate embodiment of a check valve according to the invention. Other designs of the check valve, particularly those fashioned to mimic biological valves (e.g., venous, mechanical or bioprosthetic heart valves) would suffice also.

DETAILED DESCRIPTION OF THE INVENTION

Figure 6:
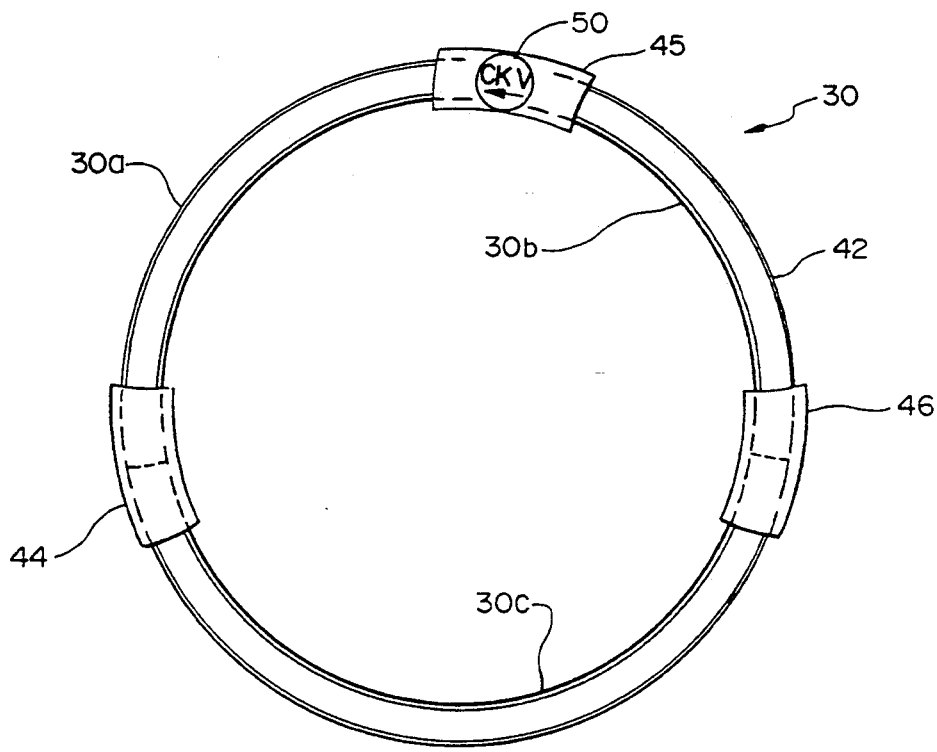
FIG. 6 is a plan view of the improved test cell of the invention showing the check valve schematically.

As already indicated, a closed loop test cell containing blood has been used previously for studying and testing dynamic blood-biomaterial interactions by simulating the flow under conditions of oscillation of a closed loop test cell.

In the improved device of the invention, it has been determined that pulsatile flow conditions can be more accurately replicated by incorporating a check valve into the test loop and imparting either the oscillatory motion about a fixed point as described by Clark or a new start-stop motion to the test cell while rotating it in one direction only. Additionally, optimum accuracy in physiological flow simulation is best obtained when the check valve in the tubular test vehicle is of hemodynamic and physiological design. As mentioned, this modified test vehicle can be utilized for simulating pulsatile blood flow in the mode shown in the prior art, i.e., with oscillatory motion as well as in the new motional mode according to the present invention.

More specifically, the improved apparatus is shown in the Figures of the drawing in which FIGS. 1 and 2 show the overall apparatus in some schematic detail. The apparatus includes, as shown in FIGS. 1 and 2, a base housing 10 which contains a gear box 12 driven by an electrical motor 14. Electrical motor 14 is of the type known as a stepper motor with microstepping function or capacity which imparts a specific and repeatable start-stop mode of rotation through gear box 12 to a vertical shaft 16. Shaft 16 is connected to gear box 12 so as to be rotated about its longitudinal axis by the gear box. Stepper motor 14 is preferably of the type obtained from Compumotor Division of Parker Hannifin Corporation, Rohnert Park, Calif. 94928, as model No. Compumotor 583-93 brushless stepper motor or analogous Superior Electric product from Superior Electric/Warner Electric-Dana Corporation, Bristol, Conn. 06010. Motor 14 may be controlled by a programmable electronic control means 15, described in more detail below with reference to the operation of the apparatus. Gear box 12 is preferably of the type obtained from Bayside Controls, Inc., of Port Washington, N.Y. 11050 as Model No. RA90-010. Other drive arrangements for imparting the preferred start-stop rotary motion to shaft 16 may be utilized as will be readily apparent to those of familiarity with the art. However, the aforementioned arrangement is presently preferred.

The ideal motion profile is one that will impart a pulsatile flow within the test loops that precisely mimics physiological i.e., mean velocity and flow profile of blood in a vessel of comparable diameter (e.g., small diameter vessel such as the femoral or popliteal). Broken down into its component elements, the physiological flow profile in a blood vessel has been described in the literature. See the article entitled "Quantitative Ultrasonographic Studies of Lower Extremity Flow Velocities in Health and Disease" by A. Fronek, M. Coel and E. F. Bernstein which appeared in *Circulation*, Vol. 53, No. 6, Jun. 1917 at p. 958. Also see *Geigy Scientific Tables*, Vol. 5, *Heart and Circulation, Eighth Revised and Enlarged Edition*, at p. 226, published by CIBA-GEIGY.

Description of the wave form or flow profile of blood within a vessel typically consists of an acceleration time ($T_{ac}$, or pulse rise time, corresponding to the rapid ejection phase of the cardiac cycle), deceleration time ($t_{dc}$, or pulse decay time, corresponding to the reduced ejection phase of the cardiac cycle), peak (systolic) forward velocity ($V_{pf}$), peak reverse velocity ($V_{pr}$), mean flow velocity ($V_{mf}$), and mean cycle time ($T_{mc}$) Diastolic time ($T_{di}$, or the time involved in rapid and reduced filling and diastasis of the cardiac cycle), is estimated from $T_{mc}=T_{ac}+T_{dc}+T_{di}$. The basic repeat element of a typical simple motion profile program may consist of a circular pulse of motion to the loop followed by a pause such that $T_{mc}=1$ second (i.e., 60 beats per minute) and $V_{pf}=40-70$ cm/s (i.e., approximately 300–500 ml/min in a 4 mm ID test loop). The pulse, for example occurring over a 300–500 ms period, can consist of a linear, exponential, or sigmoidal acceleration of the tubing to a velocity intended to approximate the $v_{pf}$. During this period, the check valve changes from an "open" to a "closed" position as the seat of the valve, which is actually part of the tubing valve assembly, causes the "closed" position to occur by movement toward the free floating valve closure member. The pause that immediately follows the pulse may last 700–500 ms. During the latter period, the test loop check valve moves rapidly from a "closed" to "open" position due to tangential fluid momentum which occurs as a result of the fluid mass acquiring the angular velocity of the loop when the check valve closes. When continuously repeated, this pattern of motion creates net and directional pulsatile flow in the fluid within the test loop. In the pause period, flow from fluid momentum comes to a peak approximating the $V_{pf}$ and then begins to dissipate via viscous drag from within the fluid, as well as drag from the wall and from the valve (approximating the $T_{ac}$ and part of the $T_{dc}$ segments of the wave form flow profile). The pulse phase of the cycle involving acceleration of the test loop to the $V_{pf}$ further contributes to the $T_{dc}$ of the fluid wave form and approximates the diastole time reflecting rapid and reduced filling and diastasis of the cardiac cycle. Actual fluid flow profiles within the loops may be further modified by creating more elaborate and advanced motion profile programs to simulate other resting and active cardiovascular conditions (i.e., and corresponding $V_{mf}$'s, shear forces, etc...). For net directional flow to occur in the test loops under such motion profiles, the prongs in a check valve of the type described herein as a preferred embodiment (see below) must face in the direction opposite that of the acceleration. If otherwise, minimal net fluid motion occurs and that which does occur more approximates that of the Clark apparatus. Motion profiles based upon oscillatory motion about a fixed point are not as sensitive with regard to valve orientation to set up net directional fluid flow.

Vertical shaft 16 is constructed and arranged to mount a tiered series of preferably disc-shaped trays 18 which are fastened to shaft 16 as shown in FIGS. 1 and 2 for rotation therewith. More details concerning the structure of trays 18 will be discussed hereinbelow in connection with FIGS. 3, 4 and 5.

As can be seen in FIG. 2, shaft 16 and trays 18 are enclosed within an enclosure 20 to contain a fluid which is utilized as a bath for temperature control purposes during operation of the apparatus. The fluid is introduced into enclosure 20 and removed therefrom by means of fittings 22 and 24, respectively, which may include valves (not shown), if desired, for flow control through the bath enclosure. Enclosure 20 includes a cover 26 through which a pin 28 may depend to aid in supporting shaft 16 as shown in FIG. 2 for its rotational movement as imparted thereto by means of the stepper motor and gear box.

Referring now to FIGS. 3, 4 and 5, a test tray is shown in detail at 18. As shown in FIG. 4, the closed loop tubular test cell 30 is carried or mounted on test tray 18 between a plurality of pin pairs 32, preferably arranged as shown in FIG. 3. Tray 18 includes a set screw and hub arrangement shown in FIG. 5 at 34 and 36, respectively for affixing and mounting tray 18 to shaft 16 and locking it thereto so as to impart the rotary motion of shaft 16 to each of the trays 18 mounted thereon. Pins 32, as best seen in FIG. 4, may take the form of bolts inserted upwardly through slots 38 in tray 18. The bolts include an upper nut 40 which may be used to lock them into position as desired within the slots. As best seen in FIG. 3, slots 38 are arranged diametrically (with respect to tray 18) in tray 18 so as to allow diametric adjustment of pins 32 to accommodate various tubular sizes of test cells 30 or to accommodate more than one test cell between the sets of pins on each of the trays 18. A main principal behind the design is that direct motion is transferred to the test loops with minimal mechanical backlash.

Figure 7:
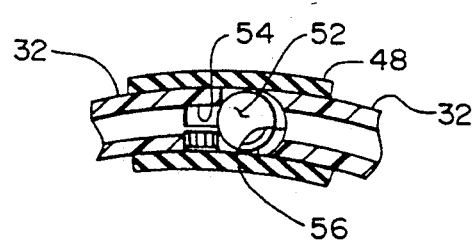
FIG. 7 is a cross-sectional view of a portion of the test cell showing a preferred embodiment of a ball check valve for use in the invention.

Referring now to FIGS. 6 and 7, the improved test cell per se is described in detail. As seen and generally indicated in FIG. 6 at 30, the test cell comprises a tubular closed loop of medical-grade test material (e.g., polyurethane, silicone, polyvinyl-chloride, polyethylene, etc.). The tubular body 42 of test cell 30 may be of one-piece tubing or, as shown, may consist of several pieces 30a, b and c, held together by external cuffs 44, 45 and 46, which may also specifically function to facilitate filling of the test cell as is known in the art (i.e., acting as injection and ejection ports). Although gum rubber is preferred for the cuffs, other materials such as silicone, and polyurethane may be used also. Many such substitute materials will be readily apparent to those familiar with this art. Within cuff 45, there is schematically indicated in FIG. 6 a check valve 50, a preferred form of which is shown in detail in FIG. 7. This preferred form comprises a ball check valve including a valve closure member in the form of a ball 52 which as shown may seat against a longitudinally slotted end 54 (providing the aforementioned prongs) of the tubing (as seen in FIG. 7) to provide an "open" position and when seated against end 56 provides a "closed" position. End 56 may be shaped in a curved fashion to receive ball 52 as shown.

For testing and operational purposes as seen in FIG. 8, test cell 30 is merely laid between pairs of pins 32 on tray 18 and held by friction and/or secured with rubber bands about the pins) in which position it will be held and subjected to the rotary motion imparted to shaft 16 by gear box 12 and stepper motor 14.

Referring to FIG. 9, an alternate check valve arrangement is shown wherein the valve closure member is a disc-shaped body 62 which is free floating between the spaced, juxtaposed ends or end portions of tubular body 32, one end of which at 64 provides a "closed" seat while the other end at 66 is slotted as indicated in FIG. 7 to provide seating prongs and an "open" position for the check valve.

In operation, the check valve-containing closed-loop is first filled with a physiological buffer to displace all air followed by displacement of the buffer by treated or untreated whole blood. The blood filled test loop is then mounted on the disc. As indicated in FIG. 2, a plurality of test cells may be mounted on the tiered disc trays in accordance with the structure of the apparatus as shown in FIGS. 1 and 2 that is, one or more per tray. The stepper motor is computer driven-programmable by a suitable control indexer/drive unit 15 (schematically shown in FIG. 1) to create pulsatile motion to the disc/loop setup. Such a control is available from Compumotor or an analogous product from Superior Electric (Compumotor Model SX-6 Indexer/Drive or the Superior Electric equivalent). This unit may be modified with simple program selection, on-off (start-stop), and timer features to make it more user-friendly. Thus, a directional and controllable flow of blood is created in the blood in the test loop via the check valve and rotational action. Given such a simulated pulsatile flow arrangement, special tests may be performed on both the material or device and the blood following contact/flow over specified conditions and times. The improved apparatus has the advantages of (1) screening novel biomaterials, vascular devices, and surface-modified biomaterials under physiological and reproducible conditions; (2) optional programming of a variety of flow conditions; (3) high number of replicates/accurate statistics applied; (4) low hemolysis; (5) low blood volume required/test; (6) human blood testing possible; and (7) blood air interface eliminated.

Figure 10:
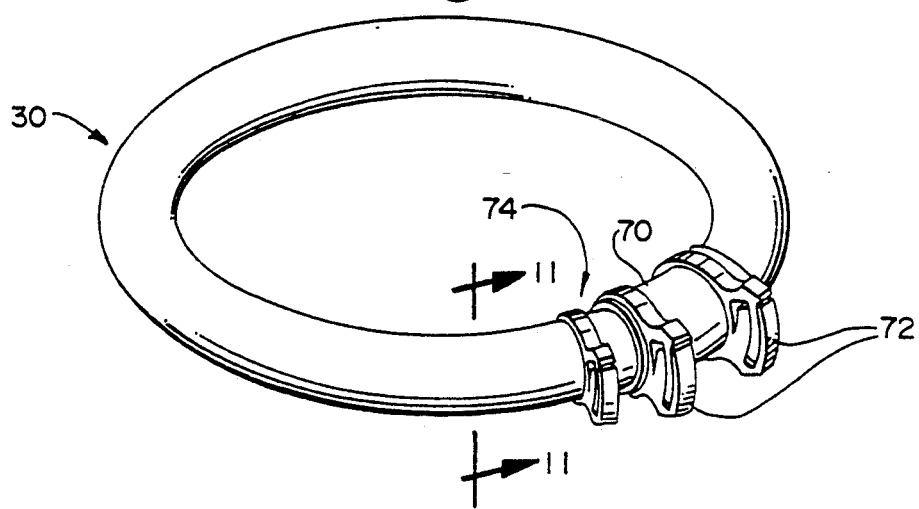
FIG. 10 is a pictorial representation of a test cell having a mechanical heart valve installed in its loop.
Figure 11:
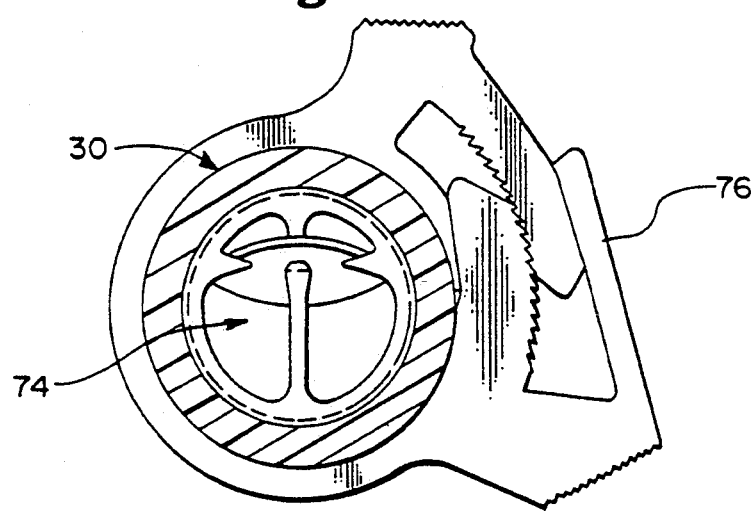
FIG. 11 is a cross-sectional view taken along lines 11—11 of FIG. 10.

As an example of a test cell having a cardiovascular device in the loop, reference is made to FIGS. 10 and 11. The loop of the test cell is held together by means of a cuff 70 as in FIGS. 6 and 8 with the aid of two plastic clips 72. The test cell 30 also includes a mechanical heart valve of the Hall type generally indicated at 74 in the test loop. Valve 74 (best seen in FIG. 11) in this instance also functions in the test cell loop as a check valve in accordance with the known manner of the operation for such valves. It is held in place by means of plastic clips 76 and operates in the known fashion as a mechanical valve for controlling blood flow.

The check valve is oriented within the tubing of the test cell to allow unidirectional flow preferably only in the direction of rotation. Any means for synchronously occluding the loop of the test cell may be utilized in place of the check valve. The use of the stepper motor with the unidirectional start-stop rotational movement more closely simulates blood flow in vessels than the oscillatory movement of the prior art apparatus lacking the check valve.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. In an in vitro apparatus for simulating physiological blood flow and for testing blood-material interactions for blood-contacting materials the apparatus including a circular, closed-loop tubular, test cell for containing blood, means for imparting oscillatory or pulsed rotational movement to the blood-containing test cell, and means for determining blood-material interaction in the test cell due to the oscillatory or pulsed rotational movement, the improvement comprising: means for synchronously occluding the test cell in coordination with the movement thereof.

2. The apparatus of claim 1 in which the synchronous means comprises a check valve in the test cell to control the direction and net flow of blood therein as the test cell is subjected to movement.

3. The apparatus of claim 2 in which the check valve is of a ball valve.

4. The apparatus of claim 2 in which the check valve is of a disc value.

5. The apparatus of claim 1 in which the check valve is an artificial heart valve prosthesis.

6. The apparatus of claim 2 in which the tubular test cell and check valve are oriented with respect to the apparatus and the rotational movement to be provided such that flow through the check valve is in a direction corresponding to the direction of rotation as provided by the apparatus.

7. The apparatus of claim 1 wherein the means for imparting directional rotation to the test cell is constructed and arranged to provide start-stop movement in unidirectional fashion.

8. The apparatus of claim 7 therein the means for imparting rotation includes a stepper motor.

9. The apparatus of claim 1 including temperature control bath means for receiving the test cell during testing.

10. In a circular closed-loop tubular test cell having means for permitting introduction of a blood-material sample to the loop of the test cell, said test cell being for use in an in vitro apparatus for simulating physiological blood flow and for testing blood-material interactions for blood-contacting materials, the apparatus including means for mounting a blood-containing test cell, means for imparting oscillatory or pulsed rotational movement to the test cell, and means for determining blood-material interaction in the test cell due to the oscillatory or pulsed rotational movement, the improvement comprising means for synchronously occluding the loop of the test cell with the movement thereof.

11. The test cell of claim 10 in which the synchronous means comprises a check valve.

12. The test cell of claim 11 wherein the check valve is of a ball valve.

13. The test cell of claim 11 wherein the check valve is a disc valve.

14. In an apparatus for simulating in vitro blood flow including a circular closed-loop, tubular test cell for receiving blood, means for imparting oscillatory or pulsed rotational movement to the test cell, and means for determining blood-material interaction in the test cell due to the oscillatory or pulsed rotational movement, the improvement comprising a vertical, rotational, axle means constructed and arranged to receive and rotate a plurality of tiered trays, each of which is adapted to receive at least one test cell, and drive means connected to the lower end of the axle means for imparting rotational movement thereto.

15. The apparatus of claim 14 wherein the drive means includes a stepper motor.

16. The apparatus of claim 15 including gear box means constructed and arranged to provide smooth and physiological shear rates while carrying the applied load, the gear box means interconnecting the stepper motor and the axle means.

17. The apparatus of claim 14 including enclosure means positioned around the axle means and tiered trays for providing a temperature control bath.

18. The apparatus of claim 14 wherein each tray includes a plurality of paired upstanding, posts for receiving a test cell on the tray, the paired posts being positioned diametrically in the trays with respect to the center of rotation thereof.

19. The apparatus of claim 18 wherein the paired posts are adjustable with respect to each other, being movable along a line coincident with the diameter of the tray.

20. The apparatus of claim 18 wherein the trays are provided with slots for receiving the posts.

21. In a circular closed-loop tubular test cell for use in an in vitro apparatus for simulating physiological blood flow and for testing blood-material interactions for blood-contacting materials, the apparatus including means for mounting a blood-containing test cell, means for imparting oscillatory or pulsed rotational movement to the test cell, and means for determining blood-material interaction in the test cell due to the oscillatory or pulsed rotational movement, the improvement wherein two tubular end portions of the tubular cell are positioned in juxtaposition with a space therebetween, a movable valve closure member is positioned within the space in such a way as to be movable from one end portion to the other between open and closed positions, and one of the tubular end portions is longitudinally notched whereby an open position is provided when the valve closure member is seated against that end portion and the other end portion is adapted to provide a seat for receiving the valve closure member whereby a closed position is provided when the valve closure member is seated thereat.

22. The test cell of claim 21 wherein the valve closure member is a ball valve.

23. The test cell of claim 21 wherein the valve closure member is a disc valve.

* * * * *